United States Patent
Eriksson

[11] Patent Number: 6,119,805
[45] Date of Patent: Sep. 19, 2000

[54] HEARING PROTECTOR ADAPTABLE TO CHAIR

[76] Inventor: Urban Eriksson, Banergatan 45, S-11522, Stockholm, Sweden

[21] Appl. No.: 09/269,225
[22] PCT Filed: Sep. 29, 1997
[86] PCT No.: PCT/SE97/01636
    § 371 Date: Mar. 23, 1999
    § 102(e) Date: Mar. 23, 1999
[87] PCT Pub. No.: WO98/14150
    PCT Pub. Date: Apr. 9, 1998

[30] Foreign Application Priority Data

Sep. 30, 1996 [SE] Sweden .................................. 9603672

[51] Int. Cl.[7] .................................................. H04R 25/00
[52] U.S. Cl. ................. 181/129; 381/71.1; 381/73.1; 381/94.1; 381/71.6; 128/864; 128/866; 128/867
[58] Field of Search .................... 181/129, 206, 181/175, 128, 126; 381/71.1, 71.6, 72, 73.1, 94.1, 118; 128/846, 857, 864, 866, 867; 84/422.1, 422.2, 423.3

[56] References Cited

U.S. PATENT DOCUMENTS

| | | |
|---|---|---|
| 713,401 | 11/1902 | Clark . |
| 1,502,666 | 7/1924 | Grady, Jr. . |
| 2,148,347 | 2/1939 | Gray ............................................. 179/1 |
| 3,156,500 | 11/1964 | Kerr ......................................... 297/391 |
| 3,780,825 | 12/1973 | Rinaldi ................................. 181/32 G |
| 4,977,600 | 12/1990 | Ziegler ....................................... 381/71 |
| 5,133,017 | 7/1992 | Cain et al. . |
| 5,545,859 | 8/1996 | Ultrich ................................... 181/129 |

FOREIGN PATENT DOCUMENTS

| | | |
|---|---|---|
| 1037901 A1 | 9/1953 | France . |
| WO 9301775 A1 | 2/1993 | WIPO . |

*Primary Examiner*—Paul Ip
*Assistant Examiner*—Edgardo San Martin
*Attorney, Agent, or Firm*—Nixon & Vanderhye

[57] ABSTRACT

In order to reduce the risk of hearing damage to musicians, for example, there is suggested according to the invention a device which comprises, firstly, a floor stand portion with a foot and a post extending upright therefrom, and, secondly, a hearing protector portion mounted on an upper portion of the post. The hearing protector portion is essentially U-shaped, as seen in plan view, in order to be able, as needed, to screen off the ears from intense sound sources located behind and to the sides. The hearing protector portion is displaceable between an advanced active position and a retracted passive position.

12 Claims, 1 Drawing Sheet

HEARING PROTECTOR ADAPTABLE TO CHAIR

BACKGROUND OF THE INVENTION

The present invention relates to a hearing protector, more particularly to a device for damping intense sound and thus reducing the risk of hearing damage to a person. Such a device is primarily intended to be able to be used by musicians, but also other sound-screening applications are conceivable.

Musicians in symphony orchestras, theater orchestras, big bands etc. often experience problems with high sound levels from sound sources behind them, which can result in permanent hearing damage for these musicians, such as a musician placed immediately in front of a source of intense sound in an orchestra, e.g. a violinist sitting in front of the brass section, i.e. trumpets, trombones etc. These wind instruments can often produce sound intensities of up to 130 dB. In order to protect the ears against such intense sound pressure, different types of protectors have been tested for the musician sitting in front, e.g. ear plugs. These, however, have the disadvantage that they also damp out sounds which the musician wishes to hear and must hear. Other methods of protecting hearing have been to place sound screens in front of the strong wind instruments or percussion instruments. Such screens can be of plexiglass, for example, and be provided with a soft damping material. Such screens, however, have a negative effect on the composite tone of the entire orchestra due to unfortunate sound reflections from the screens which have therefore had a negative effect for both the public and the players of loud instruments.

SUMMARY OF THE INVENTION

One purpose of the present invention is to avoid the disadvantages of previously known sound reflectors and to provide a sound protection device which as needed can protect the ears from high sound levels but which does not block off the sound source itself, i.e. a protector in the form of an individual screen which can screen off only the ears and damp intense sound from behind and from the sides but at the same time allow the required perception of surrounding sounds, for example, listening to the other musicians in the orchestra while playing, and without negatively affecting the composite tone of the entire orchestra. At the same time, the protector must be easily removable from an active sound-deflecting position and be capable of assuming a ready position without requiring much space.

For solving this problem, the device according to the invention comprises a device for damping intense sound and thus reducing the risk of hearing damage to a person. Such a construction provides a device which when needed can be activated by the person himself, e.g. a musician, to protect his hearing temporarily during passages with high sound levels, but which makes possible listening to the other musicians without distorsion of the sound and which can easily be moved back to the ready position. The moving of the hearing protector between its active and passive positions can be done with the head, thus requiring no manual handling, which is of particular importance to a musician.

In order to facilitate the movement of the hearing protector portion between its active and passive positions, the post is preferably pivotally joined to the foot about a horizontal axis to be able to assume a first, active advanced position, in which the hearing protector portion screens the ears of the person from sound sources lying behind and to the sides, and a second, passive position, in which the hearing protector portion is retracted from the head of the person.

It is suitable that the post be lockable in its passive position and biased towards its active, advanced position and that the post be releasable from its locked, passive position by pressing the post somewhat backwards.

The hearing protector portion itself preferably has an outer casing of a relatively hard, sound-reflecting material and an inner relatively soft sound-absorbing material.

DRAWING FIGURE DESCRIPTION

The invention will now be described in more detail below with reference to the accompanying drawings, in which.

DETAILED DESCRIPTION OF THE INVENTION

Figure 1:
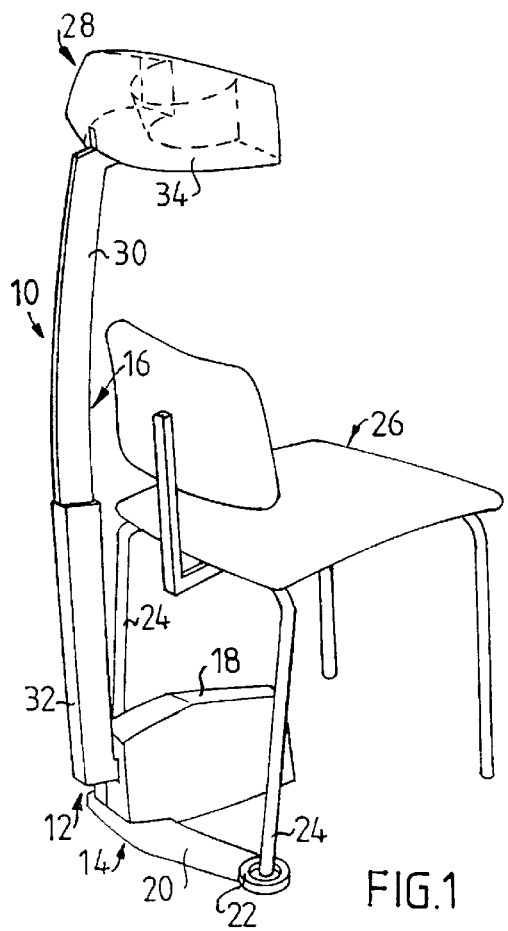
FIG. 1 is a perspective view obliquely from behind of a hearing protector device according to the present invention and a chair placed loosely thereon.

With reference to the drawings and in particular to FIG. 1, 10 generally designates a device according to the invention for reducing the risk of hearing damage to orchestra musicians. The device 10 comprises a floor stand portion 12 which has a foot 14 and a post 16 extending upright therefrom. The foot 14 consists of a housing 18 consisting of a mounting mechanism for the post 16 and a pair of supporting legs 20 extending from the housing 18, each with a respective supporting surface 22 at each outer end for receiving a pair of rear chair legs 24 of the chair 26 of the musician whose ears, as needed, will be protected from loud sound levels from orchestra instruments behind him and to his sides.

The device 10 further comprises a hearing protector portion 28 which is carried on an upper arm portion 30 of the post 16. The hearing protector portion 28 can be raised and lowered by virtue of the fact that the arm portion 30 is telescoping and can be fixed in a lower arm portion 32 of the post 16 to place the hearing protector portion 28 at head level for the particular musician.

Figure 2:
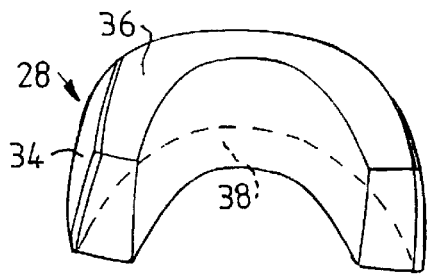
FIG. 2 is a perspective view of the hearing protector portion proper as seen from the front.

In a most preferred embodiment of the hearing protector portion 28, it has, as seen in plan view, essentially a U-shape, as best can be seen in FIG. 2, and consists of an outer casing 34 of a relatively hard, sound-reflecting material, e.g. a fiberglass reinforced plastic, and a lining 36, also U-shaped, of relatively soft, sound-absorbing material, which rests on an inwardly directed bottom wall 38 of the casing 34, which screens out reflected sound from below. The hearing protector portion 28 is dimensioned to fit relatively closely around the head from behind so that the ears can be protected from strong sound pressure from instruments placed behind and to the sides. The hearing protector portion 28 can be removable and thus interchangeably mounted on the post arm 30, and possibly be pivotally mounted for individual setting. Furthermore, the U-shaped inside of the sound-insulating lining 36 can be provided, for hygienic reasons, with a removable individual protective cover (not shown) held in place by Velcro®, for example.

Figure 4:
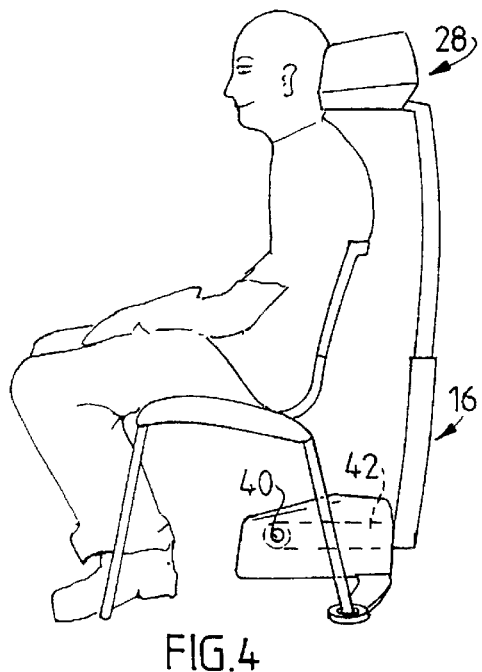
FIG. 4 is a side view of a sitting musician with a sound-deflecting device according to the invention placed behind him in a passive, ready position.
Figure 5:
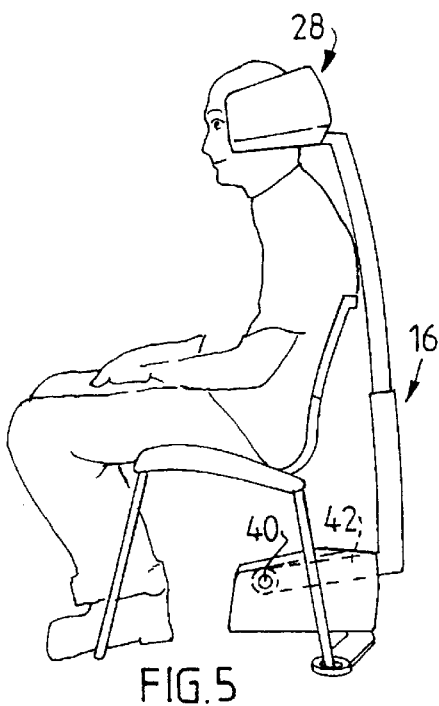
FIG. 5 shows the device in FIG. 4 in an active, advanced sound-deflecting position.

In the preferred embodiment shown in the drawing, the hearing protector portion 28 is disposed, with the aid of the floor stand portion 12 to be moved between a retracted, passive ready position, as shown in FIG. 4, and an advanced, active sound-deflecting position, as shown in FIG. 5. For this purpose, the lower arm portion 32 of the post 16 is pivotally mounted in the housing 18 about a horizontal axis 40 (FIGS. 4 and 5) located at a forward portion of an inwardly directed portion 42 of the arm 32, so that the pivot axis 40 of the post 16 and thus of the hearing protector portion 28 will be located relatively close to the pivot point for the upper torso of the musician sitting on the chair 26. In the passive position shown in FIG. 4, the post 16 is retained in its position by means of a locking mechanism (not shown), which can be released by exerting a rearwardly directed pressure on the hearing protector portion 28 with the head, whereupon the post 16 is pivoted a short distance clockwise, as seen in FIG. 4. By virtue of the fact that the post 16 is spring-biased in the counter-clockwise direction, as seen in FIGS. 4 and 5, by means of a spring element (not shown), the post, after releasing the lock, will pivot in the counter-clockwise direction so far that the hearing protector portion 28 will assume a suitable active, sound-deflecting position around the head of the musician, as shown in FIG. 5. In order to return the hearing protector portion 28 to its passive ready position, all that is required is that the hearing protector 28 and the post 16 be pushed backwards to the position shown in FIG. 4, and the lock (not shown) is arranged to be activated to hold the post 16 in this position. When the musician once again wishes to protect himself from high sound levels, he will press this hearing protector portion 28 somewhat backwards with his head, to first release the lock on the post, before it is brought to the active position shown in FIG. 5 with the aid of the biasing spring.

Figure 3:
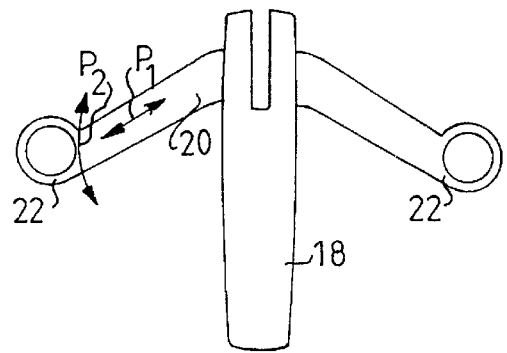
FIG. 3 is a plan view of the foot of the device according to the invention.

As was mentioned above, the foot 14 has a pair of supporting legs 20 with chair leg supporting surfaces 22 on which the rear chair legs 24 of the chair 26 can be placed to hold the floor stand 12 securely in place during use. In order to adjust the supporting surfaces 22 to various chair leg spacing, the supporting legs 20 can be adjustable in the directions of the arrows $P_1$ and/or $P_2$ in FIG. 3. In the embodiment shown the housing 18 is directed forwards beneath the chair, which means that the device 10 will take up a minimum of space behind the chair and will therefore not encroach on the space available for movement for the musician sitting behind the musician in question.

Even if the embodiment described above of the device according to the invention is operated manually with the head, it is of course also conceivable within the scope of the invention to provide a device with electrical drive means, for example, for moving the hearing protector portion between its active and passive positions, with the drive means being controlled by a foot pedal, for example.

What is claimed is:

1. A device for damping intense sound and reducing the risk of hearing damage to a person, comprising a floor stand portion with a foot and a post extending upright therefrom, and a hearing protector portion mounted on an upper portion of the post, said hearing protector portion having a generally horizontal, substantially U-shaped configuration, and being dimensioned to fit relatively closely around the head of the user from behind the user, said hearing protector portion being movable by the user between an active, advanced position, in which the hearing protector portion protects the ears of the user from sound sources lying behind and to the sides of the user, and a passive, retracted position, in which the hearing protector portion is retracted from the head of the user, said post being pivotally joined to the foot about a horizontal axis.

2. A device according to claim 1 wherein the post is lockable in its passive position and is biased towards its active, advanced position.

3. A device according to claim 2 wherein the post is releasable from its locked, passive position by moving the post a short distance backwards.

4. A device according to claim 1 wherein the length of the post is variable.

5. A device according to claim 4 wherein the post includes telescopically extendable and retractable arms.

6. A device according to claim 1 wherein the hearing protector portion has an outer casing of a relatively hard, sound-reflecting material, and a lining portion of a relatively soft, sound-insulating material.

7. A device according to claim 6 wherein the casing has an essentially U-shaped bottom wall for supporting the lining portion and deflecting sound reflected from below.

8. A device for damping intense sound and reducing the risk of hearing damage to a person, comprising a floor stand portion with a foot and a Post extending upright therefrom, and a hearing protector portion mounted on an upper portion of the post, said hearing protector portion having a generally horizontal, substantially U-shaped configuration, and being dimensioned to fit relatively closely around the head of the user from behind the user, said hearing protector portion being movable by the user between an active, advanced position, in which the hearing protector portion protects the ears of the user from sound sources lying behind and to the sides of the user, and a passive, retracted position, in which the hearing protector portion is retracted from the head of the user, said foot having at least two laterally extending supporting legs each with an upwardly facing supporting surface for a pair of chair legs.

9. A device according to claim 8 wherein the supporting legs are adjustably mounted in the foot to adapt the supporting surfaces to various chair leg spacings.

10. A device for damping intense sound and reducing the risk of hearing damage to a person, comprising a floor stand portion with a foot and a post extending upright therefrom, and a hearing protector portion mounted on an upper portion of the post, said hearing protector portion having a generally horizontal, substantially U-shaped configuration, and being dimensioned to fit relatively closely around the head of the user from behind the user, said hearing protector portion being movable by the user between an active, advanced position, in which the hearing protector portion protects the ears of the user from sound sources lying behind and to the sides of the user, and a passive, retracted position, in which the hearing protector portion is retracted from the head of the user, said post being pivotally joined to the foot enabling the post for movement between the advanced and retracted positions, the post including telescopically extendable and retractable arms.

11. A device according to claim 10 wherein the foot has at least two laterally extending supporting legs each with an upwardly facing supporting surface for a pair of chair legs.

12. A device according to claim 11 wherein the supporting legs are adjustably mounted in the foot to adapt the supporting surfaces to various chair leg spacings.

* * * * *